United States Patent
Shang et al.

(10) Patent No.: US 10,241,345 B2
(45) Date of Patent: Mar. 26, 2019

(54) LASER SYSTEM PRESERVING POLARIZATION THROUGH A FREELY MOVABLE BEAM DELIVERY SYSTEM

(71) Applicant: Candela Corporation, Wayland, MA (US)

(72) Inventors: Xiaoming Shang, Lexington, MA (US); Jayant Bhawalkar, Auburndale, MA (US)

(73) Assignee: Candela Corporation, Wayland, MA (US)

( * ) Notice: Subject to any disclaimer, the term of this patent is extended or adjusted under 35 U.S.C. 154(b) by 12 days.

(21) Appl. No.: 15/678,284

(22) Filed: Aug. 16, 2017

(65) Prior Publication Data

US 2018/0074338 A1    Mar. 15, 2018

Related U.S. Application Data

(60) Provisional application No. 62/394,231, filed on Sep. 14, 2016.

(51) Int. Cl.
| | |
|---|---|
| *G02B 27/28* | (2006.01) |
| *G02B 26/08* | (2006.01) |
| *A61B 18/20* | (2006.01) |
| *A61N 5/06* | (2006.01) |
| *A61N 5/067* | (2006.01) |
| *A61N 5/073* | (2006.01) |

(52) U.S. Cl.
CPC ............ *G02B 27/283* (2013.01); *A61B 18/20* (2013.01); *G02B 26/0816* (2013.01); *A61B 18/201* (2013.01); *A61B 2018/20359* (2017.05); *A61N 5/0616* (2013.01); *A61N 2005/067* (2013.01); *A61N 2005/073* (2013.01)

(58) Field of Classification Search
CPC .......... A61B 18/20; A61B 2018/20359; A61B 18/201; A61N 2005/073; A61N 2005/067; A61N 5/0616; G02B 27/283; G02B 26/0816
USPC ................................................. 359/618, 629
See application file for complete search history.

(56) References Cited

U.S. PATENT DOCUMENTS

2016/0334570 A1* 11/2016 Hertwig ................ G02B 6/024

* cited by examiner

*Primary Examiner* — Tuyen Tra
(74) *Attorney, Agent, or Firm* — Manelli Selter PLLC; Edward J. Stemberger

(57) ABSTRACT

Disclosed is an apparatus and a method to preserve linearly polarized laser beam when it passes through a freely twisting beam delivery system such as an articulated arm. The polarization of the output beam from the delivery system will be stable and the same as the polarization of the input beam to the delivery system, and can be used to pump anisotropic laser crystals as well as nonlinear optical crystals.

11 Claims, 1 Drawing Sheet

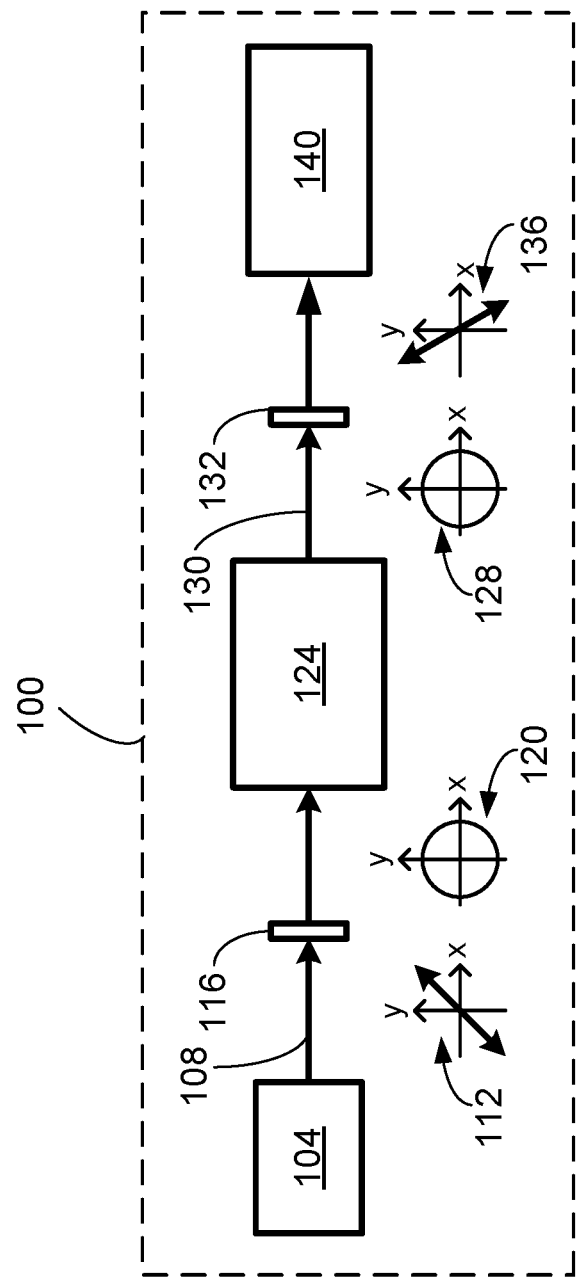

LASER SYSTEM PRESERVING POLARIZATION THROUGH A FREELY MOVABLE BEAM DELIVERY SYSTEM

TECHNOLOGY FIELD

The present system relates to laser beam delivery systems and in particular to beam delivery systems that employ multiple mirrors, which move in order to support a plane polarized laser beam to be manipulated spatially while maintaining the beam's plane of polarization fixed.

BACKGROUND

Lasers are increasingly used in different applications ranging from metal cutting to skin treatment and cosmetic procedure. Often in these applications, the laser beam must be manipulated spatially in order to move the beam over the area to be treated. In the case of metal cutting, the beam may need to be move over the metal to achieve a desired cutting path over the contours of the work piece. In the case of skin treatments, the beam may need to be moved in order to follow the contour of a body part to cover an area of the body with the beam. The beam delivery system often used in these applications consists of multiple mirrors which can rotate and move. An example of such a beam delivery system is an articulated arm system. In such a system, as beam is manipulated, the mirrors rotate and move. A consequence of the movement of the mirrors in such a system is that the delivered beam is rotated around its axis, and the amount of rotation depends on the position and orientation of the mirrors. A plane polarized beam going through such a system will emerge with its polarization plane rotated by a varying amount depending of the position and orientation of the mirrors, so that as the beam is manipulated the plane of polarization of the output beam will rotate continuously.

In some instances it is beneficial to maintain the polarization plane fixed. In the case of metal cutting, it is well known that the speed of cutting that can be achieved with a given amount of beam power is dependent on the polarization of the beam relative to the direction of the beam travel over the work piece. In the case of skin treatments, it is often advantageous to be able to convert the wavelength of the beam for treating different dermatologic conditions. Wavelength conversion can be accomplished by using the beam to pump another laser medium to generate a second laser beam, or by nonlinear frequency conversion techniques. In both of these, the conversion process often require that the polarization of the beam be fixed with respect to an optical axis of the laser medium to be pumped or an optical axis of the non-linear medium used. In this case, if the wavelength conversion is more conveniently done after the beam is put through an articulated arm, then the uncontrolled rotation of the polarization of the beam as the arm is manipulated will preclude such a system.

This present apparatus is intended to support a plane polarized beam to be propagated through a beam manipulation system consisting of multiple moveable mirrors while maintaining its plane of polarization constant.

Glossary

As used in the current disclosure the term articulated arm means an assembly of a number of mirrors and mechanical levers or arms connected between them by rotary joints. Articulated arms support a large number of independent motions in which the end effector can move in a plurality of directions.

As used in the current disclosure the term laser pumping means an act of energy transfer from the pumping source into the gain medium of a pumped laser or nonlinear optical crystal. For the former case, the energy is absorbed in the gain medium, producing excited states in its atoms. For the latter case, the pump energy converts to the laser energies of other wavelengths following phase matching conditions.

Polarization preserving mirror are mirrors that upon reflection of a polarized incident beam do not change the polarization state of the reflected beam. Typically, such mirrors represent a reflective layer coated by a transparent layer.

As used in the current disclosure the term linearly or plane polarized light also includes elliptically polarized light which can be transmitted through a linear polarizer with minimal energy loss.

SUMMARY

Disclosed is an apparatus and a method to preserve linearly polarized laser beam when it passes through a freely twisting beam delivery system such as an articulated arm. The polarization of the output beam from the delivery system will be fixed relative to an optical element or target at the output of the system such that the output beam can be used to pump anisotropic laser crystals (such as rare-earth or transition-metal doped YVO4, YAP, YLF, Sapphire, etc.) to achieve efficient lasing operation as well as to support efficient nonlinear frequency conversion.

LIST OF DRAWINGS

FIG. 1 is a schematic example of the system for preserving laser beam polarization through a movable beam delivery system.

DESCRIPTION

The present apparatus is intended to support a plane polarized beam to be propagated through a beam manipulation system consisting of multiple moveable mirrors while maintaining its plane of polarization constant.

The pumping efficiency of a laser pumping beam is among others determined by its polarization state. The authors of the current disclosure have experimentally proven that pumping of anisotropic laser crystals by linearly polarized laser light results in a higher pumping efficiency.

The laser system among other components includes a moveable delivery system with polarization preserving mirrors (PPMS) and two quarter-wave plates (QWP1 and QWP2). The coatings for polarization preserving mirrors are designed such that the phase shift between polarization component S and P is zero or $\pi$. As the delivery system moves around in space the mirrors in the delivery system change their orientation, but the polarization orientation of the laser pumping beam is retained. The quarter-wave plates are oriented such that the laser pumping beam polarization is transformed from linear to circular and vice versa, as it may be required.

Laser system 100 includes a laser light or laser beam source 104 configured to emit a first beam of polarized light 108. The polarization of first beam of polarized light 108, as schematically shown by diagram 112, is a linear or plane polarization. A beam delivery system 124 is configured to receive emitted first beam of polarized light 108 and direct the received first beam of polarized light 108 to a target system 140, the beam delivery system 124 is also configured to transmit the first beam 108 and support change in direction of received first beam of polarized light 108 to a desired point on a target system 140.

Beam delivery system 124 is an articulated arm including multiple arms or elbows and mirrors configured to direct the first beam of polarized light 108 to a desired point on a target system 140 by rotation around one or more rotary joints connecting the arms or elbows. The mirrors of the articulated arm would typically be polarization preserving mirrors (PPMS). The coating of polarization preserving mirrors of the beam delivery system 124 are designed to introduce a phase difference of zero radians or π (pi) radians upon reflection from that mirror. Such design preserves the polarization plane of the incident polarized light. Beam delivery system 124 in addition to rotation around one or more rotary joints connecting the arms or elbows supports linear movement or displacement of the arms (elbows) and mirrors.

System 100 further includes two quarter-wave plates (QWP1 and QWP2). A first quarter wave plate 116 is installed in laser beam path 108 between laser light source 104 and beam delivery system 124. In some examples, first quarter wave plate 116 could be installed just at the entrance of beam delivery system 124. The first quarter wave plate 116 is oriented and configured to receive the first beam of polarized light 108 and transform linearly polarized light to circularly polarized light, as shown by diagram 120.

Due to the polarization preserving characteristics of the mirrors within the delivery system, the polarization of the circularly polarized input laser beam will be maintained all way through when it is reflected off from the mirrors within the delivery system. Therefore a light (laser) beam that exits the beam delivery system 124 will still be circularly polarized laser beam. As the beam delivery system 124 moves around in space the mirrors in the delivery system change their orientation, but the circular polarization of the beam is retained.

A second quarter wave plate 132 is installed in laser beam or light 130 path between the beam delivery system 124 and the target 140. The second quarter wave plate 132 is configured to receive polarized laser beam 130 exiting beam delivery system 124 to form a linearly polarized laser beam as shown by diagram 136. To optimize the laser pumping efficiency the laser pumping beam polarization could be aligned with preferable laser crystal axis or to maximize nonlinear frequency conversion efficiency by satisfying phase matching condition.

Target system 140 could be one of a group of systems comprising a second laser or a nonlinear crystal to be pumped by the second beam 130 of polarized light. Target system 140 generally needs the beam of polarized light 130 to maintain stable its polarization orientation. The rotation of QWP2 140 can change the polarization orientation of the linearly polarized output beam such that the pumping efficiency or nonlinear frequency conversion efficiency will be optimized.

It is to be understood that the foregoing illustrative examples have been provided merely for the purpose of explanation and are in no way to be construed as limiting of the laser system and method. Although the examples have been described herein with reference to particular laser system structure and methods of using the laser system neither of these is intended to be limited to the particulars disclosed herein. Rather, the current disclosure extends to all functionally equivalent laser system structures, methods and uses, such as are within the scope of the appended claims.

PART LIST

100—Laser system
104—Laser light source
108—First polarized beam
112—Diagram indicating polarization of the first polarized light beam
116—First quarter wave plate
120—Diagram indicating polarization of the first polarized light beam after the first quarter wave plate
124—Beam delivery system
128—Diagram indicating polarization of the polarized light beam (second beam) after the beam delivery system
130—Second polarized beam
132—Second quarter wave plate
136—Diagram indicating polarization of the polarized light beam after the beam delivery system
140—Target system that requires linearly polarized light beam

What is claimed is:

1. A laser system comprising:
a laser light source configured to emit a first beam of plane polarized light;
a beam delivery system configured to receive emitted first beam of plane polarized light and direct received first beam of plane polarized light to a target, the beam delivery system configured to support change in direction and position of received first beam of plane polarized light to a desired point on a target while maintaining the plane of polarization of the delivered beam on the target fixed; and
wherein the beam delivery system contains mirrors configured to introduce a phase difference of zero radians or pi radians upon reflection from that mirror to preserve a polarization plane of the first beam of polarized light.

2. The laser system according to claim 1 wherein the beam delivery system is an articulated arm including multiple arms or elbows and mirrors configured to direct the beam to a desired point on a target system by rotation around one or more rotary joints connecting the arms or elbows.

3. The laser system according to claim 1 wherein a first quarter wave plate is installed in laser beam path between the laser light source and the beam delivery system, the first quarter wave plate is configured to receive the a first beam of plane polarized light and convert the plane polarized light to circularly polarized light.

4. The laser system according to claim 3 wherein a second quarter wave plate is installed between the beam delivery system and the target, the second quarter wave plate is configured to receive a circularly polarized laser beam exiting the beam delivery system to form a plane polarized laser beam.

5. The laser system according to claim 3 wherein the second quarter wave plate is rotated to optimize the laser pumping efficiency by aligning a laser pumping beam polarization with preferable laser crystal axis or to maximize nonlinear frequency conversion efficiency by satisfying phase matching condition.

6. The laser system according to claim 1 wherein the target is one of a group of targets comprising a second laser or a nonlinear crystal to be pumped by the first beam of plane polarized light and pumped target needs the plane of polarization of the light to stay fixed.

7. The laser system according to claim 1 wherein the beam delivery system in addition to rotation around one or more rotary joints connecting arms supports linear displacement of the arms or elbows and mirrors.

8. The laser system according to claim 1 wherein the beam delivery system is configured to transmit the first beam of polarized light to the target.

9. A method of providing a plane polarized laser light comprising:

operating a laser light source to emit a first beam of plane polarized light;

providing a beam delivery system configured to receive emitted first beam of plane polarized light and direct received first beam of polarized light to a target and wherein the beam delivery system includes a number of mirrors coated by a polarization preserving coating; and using a first and second quarter wave plates with a first quarter wave plate located before the beam delivery system and a second plate located after the beam delivery system to transform polarization orientation of a polarized laser beam.

10. The method according to claim 9 also employing the first quarter wave plate installed in laser beam path between the laser light source and the beam delivery system, to receive the a first beam of polarized light and convert linearly polarized light to circularly polarized light.

11. The method according to claim 9 also employing the second quarter wave plate installed between the beam delivery system and a target system to receive circularly polarized laser beam exiting the beam delivery to form a linearly polarized laser beam.

\* \* \* \* \*